(12) United States Patent
Johnson et al.

(10) Patent No.: US 7,396,679 B2
(45) Date of Patent: Jul. 8, 2008

(54) ONCOLYTIC ADENOVIRUS

(75) Inventors: Leisa Johnson, Lafayette, CA (US); Ali Fattaey, San Francisco, CA (US); Terry Hermiston, Corte Madera, CA (US); Yuqiao Shen, Orinda, CA (US); Sylvie Laquerre, Conshohocken, PA (US)

(73) Assignee: Onyx Pharmaceuticals, Inc., Emeryville, CA (US)

( * ) Notice: Subject to any disclaimer, the term of this patent is extended or adjusted under 35 U.S.C. 154(b) by 261 days.

(21) Appl. No.: 10/303,598

(22) Filed: Nov. 25, 2002

(65) Prior Publication Data

US 2004/0151696 A1 Aug. 5, 2004

Related U.S. Application Data

(63) Continuation-in-part of application No. 09/714,409, filed on Nov. 14, 2000, now Pat. No. 7,001,596.

(60) Provisional application No. 60/165,638, filed on Nov. 15, 1999.

(51) Int. Cl.
*C12N 15/00* (2006.01)

(52) U.S. Cl. .................................................. 435/320.1
(58) Field of Classification Search ............... 424/93.2; 435/320.1
See application file for complete search history.

(56) References Cited

U.S. PATENT DOCUMENTS 5,998,205 A * 12/1999 Hallenbeck et al. ......... 435/325
2001/0053352 A1* 12/2001 Yu et al. ..................... 424/93.6

FOREIGN PATENT DOCUMENTS

WO    WO 98/13508    * 4/1998

* cited by examiner

*Primary Examiner*—Peter Paras, Jr.
*Assistant Examiner*—David A. Montanari
(74) *Attorney, Agent, or Firm*—Gregory Giotta; Gary R. Fabian

(57) ABSTRACT

Viral vectors and methods of making such vectors are described that preferentially kill neoplastic but not normal cells, the preferred vector being an adenovirus that has the endogenous promoters in the E1A and/or E4 regions substituted with a tumor specific promoter which is preferably E2F responsive.

16 Claims, 6 Drawing Sheets

SEQUENCE LISTING

<160> NUMBER OF SEQ ID NOS: 25

<210> SEQ ID NO 1
<211> LENGTH: 35
<212> TYPE: DNA
<213> ORGANISM: Artificial Sequences
<220> FEATURE:
<223> OTHER INFORMATION: Adenovirus

<400> SEQUENCE: 1
gctggtgccg tctcgagtgg tgtttttta atagg         35

<210> SEQ ID NO 2
<211> LENGTH: 35
<212> TYPE: DNA
<213> ORGANISM: Artificial Sequences
<220> FEATURE:
<223> OTHER INFORMATION: Adenovirus

<400> SEQUENCE: 2
cctattaaaa aaacaccact cgagacggca ccagc         35

<210> SEQ ID NO 3
<211> LENGTH: 26
<212> TYPE: DNA
<213> ORGANISM: Artificial Sequences
<220> FEATURE:
<223> OTHER INFORMATION: Adenovirus

<400> SEQUENCE: 3
gggcggagta actagtatgt gttggg         26

<210> SEQ ID NO 4
<211> LENGTH: 26
<212> TYPE: DNA
<213> ORGANISM: Artificial Sequences
<220> FEATURE:
<223> OTHER INFORMATION: Adenovirus

<400> SEQUENCE: 4
cccaacacat actagttact ccgccc         26

<210> SEQ ID NO 5
<211> LENGTH: 37
<212> TYPE: DNA
<213> ORGANISM: Artificial Sequences
<220> FEATURE:
<223> OTHER INFORMATION: Adenovirus

<400> SEQUENCE: 5
gtgagcacta gtcgcctggt accatccgga caaagcc         37

<210> SEQ ID NO 6
<211> LENGTH: 34
<212> TYPE: DNA
<213> ORGANISM: Artificial Sequences
<220> FEATURE:

<223> OTHER INFORMATION: Adenovirus

<400> SEQUENCE: 6
gtgagcctcg agctcgatcc cgctccgccc ccgg            34

<210> SEQ ID NO 7
<211> LENGTH: 31
<212> TYPE: DNA
<213> ORGANISM: Artificial Sequences
<220> FEATURE:
<223> OTHER INFORMATION: Adenovirus

<400> SEQUENCE: 7
gctaggatcc gaagggattg acttactcac t            31

<210> SEQ ID NO 8
<211> LENGTH: 31
<212> TYPE: DNA
<213> ORGANISM: Artificial Sequences
<220> FEATURE:
<223> OTHER INFORMATION: Adenovirus

<400> SEQUENCE: 8
gctagaattc ctcttcatcc tcgtcgtcac t            31

<210> SEQ ID NO 9
<211> LENGTH: 20
<212> TYPE: DNA
<213> ORGANISM: Artificial Sequences
<220> FEATURE:
<223> OTHER INFORMATION: Adenovirus

<400> SEQUENCE: 9
ggtgacgtag gttttagggc            20

<210> SEQ ID NO 10
<211> LENGTH: 21
<212> TYPE: DNA
<213> ORGANISM: Artificial Sequences
<220> FEATURE:
<223> OTHER INFORMATION: Adenovirus

<400> SEQUENCE: 10
gccataacag tcagccttac c            21

<210> SEQ ID NO 11
<211> LENGTH: 35
<212> TYPE: DNA
<213> ORGANISM: Artificial Sequences
<220> FEATURE:
<223> OTHER INFORMATION: Adenovirus

<400> SEQUENCE: 11
gtgagcggat ccgctcgatc ccgctccgcc cccgg            35

<210> SEQ ID NO 12
<211> LENGTH: 37
<212> TYPE: DNA
<213> ORGANISM: Artificial Sequences
<220> FEATURE:
<223> OTHER INFORMATION: Adenovirus

<400> SEQUENCE: 12
gtgagcaagc ttcgcctggt accatccgga caaagcc            37

<210> SEQ ID NO 13
<211> LENGTH: 31
<212> TYPE: DNA
<213> ORGANISM: Artificial Sequences
<220> FEATURE:
<223> OTHER INFORMATION: Adenovirus

<400> SEQUENCE: 13
cgcggaattc ttttggattg aagccaatat g                           31

<210> SEQ ID NO 14
<211> LENGTH: 30
<212> TYPE: DNA
<213> ORGANISM: Artificial Sequences
<220> FEATURE:
<223> OTHER INFORMATION: Adenovirus

<400> SEQUENCE: 14
cagtcccggt gtcggatccg ctcggaggag                             30

<210> SEQ ID NO 15
<211> LENGTH: 30
<212> TYPE: DNA
<213> ORGANISM: Artificial Sequences
<220> FEATURE:
<223> OTHER INFORMATION: Adenovirus

<400> SEQUENCE: 15
ctcctccgag cggatccgac accgggactg                             30

<210> SEQ ID NO 16
<211> LENGTH: 30
<212> TYPE: DNA
<213> ORGANISM: Artificial Sequences
<220> FEATURE:
<223> OTHER INFORMATION: Adenovirus

<400> SEQUENCE: 16
gcgggaccac cgggtgtatc tcaggaggtg                             30

<210> SEQ ID NO 17
<211> LENGTH: 20
<212> TYPE: DNA
<213> ORGANISM: Artificial Sequences
<220> FEATURE:
<223> OTHER INFORMATION: Adenovirus

<400> SEQUENCE: 17
gcattctcta gacacaggtg                                        20

<210> SEQ ID NO 18
<211> LENGTH: 25
<212> TYPE: DNA
<213> ORGANISM: Artificial Sequences
<220> FEATURE:
<223> OTHER INFORMATION: Adenovirus

<400> SEQUENCE: 18
gggcgtaacc gagtaagatt tggcc                                  25

<210> SEQ ID NO 19
<211> LENGTH: 31
<212> TYPE: DNA
<213> ORGANISM: Artificial Sequences
<220> FEATURE:
<223> OTHER INFORMATION: Adenovirus

```
<400> SEQUENCE: 19
ggcagataat atgtctcatt ttcagtcccg g                              31

<210> SEQ ID NO 20
<211> LENGTH: 31
<212> TYPE: DNA
<213> ORGANISM: Artificial Sequences
<220> FEATURE:
<223> OTHER INFORMATION: Adenovirus

<400> SEQUENCE: 20
gctaggatcc aagggattg acttactcac t                               31

<210> SEQ ID NO 21
<211> LENGTH: 31
<212> TYPE: DNA
<213> ORGANISM: Artificial Sequences
<220> FEATURE:
<223> OTHER INFORMATION: Adenovirus

<400> SEQUENCE: 21
gctagaattc ctcttcatcc tcgtcgtcac t                              31

<210> SEQ ID NO 22
<211> LENGTH: 21
<212> TYPE: DNA
<213> ORGANISM: Artificial Sequences
<220> FEATURE:
<223> OTHER INFORMATION: Adenovirus

<400> SEQUENCE: 22
gccataacag tcagccttac c                                         21

<210> SEQ ID NO 23
<211> LENGTH: 20
<212> TYPE: DNA
<213> ORGANISM: Artificial Sequences
<220> FEATURE:
<223> OTHER INFORMATION: Adenovirus

<400> SEQUENCE: 23
ggtgacgtag gttttagggc                                           20

<210> SEQ ID NO 24
<211> LENGTH: 24
<212> TYPE: DNA
<213> ORGANISM: Artificial Sequences
<220> FEATURE:
<223> OTHER INFORMATION: Adenovirus

<400> SEQUENCE: 24
cctttatcca gtgcattgac tggg                                      24

<210> SEQ ID NO 25
<211> LENGTH: 20
<212> TYPE: DNA
<213> ORGANISM: Artificial Sequences
<220> FEATURE:
<223> OTHER INFORMATION: Adenovirus

<400> SEQUENCE: 25
ggagaaagtt tgcagccagg                                           20
```

ONCOLYTIC ADENOVIRUS

This application is a continuation-in-part of U.S. patent application Ser. No. 09/714,409 filed Nov. 14, 2000, now U.S. Pat. No. 7,001,596, which in turn claims priority from U.S. Provisional Application No. 60/165,638, filed Nov. 15, 1999.

FIELD OF THE INVENTION

This invention relates to adenovirus vectors, and to methods for making and using such vectors. More particularly, it relates to improved adenovirus vectors containing mutations and substitutions in the promoters of the E1A and/or the E4 regions which confer substantial tumor cell specific oncolytic activity.

BACKGROUND

From the early part of this century, viruses have been used to treat cancer. The approach has been two-fold; first, to isolate or generate oncolytic viruses that selectively replicate in and kill neoplastic cells, while sparing normal cells. Investigators initially used wild type viruses, and this approach met with some, albeit, limited success. While oncolysis and slowing of tumor growth occurred with little or no damage to normal tissue, there was no significant alteration in the course of the disease. See, Smith et al., Cancer 9: 1211-1218 (1956), Cassel, W. A. et al., Cancer 18: 863-868 (1965), Webb, H. E. et al., Lancet 1: 1206-1209 (1966). See, also, Kenney, S and Pagano, J. J. Natl. Cancer Inst., vol. 86, no. 16, p. 1185 (1994).

More recently, and because of the reoccurrence of disease associated with the limited efficacy of the use of wild type viruses, investigators have resorted to using recombinant viruses that can be delivered at high doses, and that are replication competent in neoplastic but not normal cells. Such viruses are effective oncolytic agents in their own right, and further, can be engineered to carry and express a transgene that enhances the anti neoplastic activity of the virus. An example of this class of viruses is an adenovirus that is mutant in the E1B region of the viral genome. See, U.S. Pat. No. 5,677, 178, and Bischoff, J. R., D. H. Kirn, A. Williams, C. Heise, S. Horn, M. Muna, L. Ng, J. A. Nye, A. Sampson-Johannes, A. Fattacy, and F. McCormick. 1996, Science. 274: 373-6.

It is important to distinguish the use of replication competent viruses, with or without a transgene for treating cancer, from the second approach that investigators have used, which is a non-replicating virus that expresses a transgene. Here the virus is used merely as a vehicle that delivers a transgene which, directly or indirectly, is responsible for killing neoplastic cells. This approach has been, and continues to be the dominant approach of using viruses to treat cancer. It has, however, met with limited success, and it appears to be less efficacious than replicating viruses. Nevertheless, foreign genes have been inserted into the E1 region (see McGrory, Virology 163: 614-17 (1988)), the E3 region (see Hanke, Virology 177: 437-44 (1990) and Bett, J. Virol. 67: 5911-21 (1993)) or into the E3 region of an E1 deleted vector.

As mentioned above, to avoid damage to normal tissues resulting from the use of high dose viral therapy it is preferred that the virus have a mutation that facilitates its replication, and hence oncolytic activity in tumor cells, but renders it essentially harmless to normal cells. This approach takes advantage of the observation that many of the cell growth regulatory mechanisms that control normal cell growth are inactivated or lost in neoplastic cells, and that these same growth control mechanisms are inactivated by viruses to facilitate viral replication. Thus, the deletion or inactivation of a viral gene that inactivates a particular normal cell growth control mechanism will prevent the virus from replicating in normal cells, but such viruses will replicate in and kill neoplastic cells that lack the particular growth control mechanism.

For example, normal dividing cells transiently lack the growth control mechanism, retinoblastoma tumor suppressor, that is lacking in and associated with unrestricted growth in certain neoplastic cells. The loss of retinoblastoma tumor suppressor gene (RB) gene function has been associated with the etiology of various types of tumors. The product of this tumor suppressor gene, a 105 kilodalton polypeptide called pRB or p105, is a cell-cycle regulatory protein. The pRB polypeptide inhibits cell proliferation by arresting cells at the $G_1$ phase of the cell cycle. The pRB protein is a major target of several DNA virus oncoproteins, including adenovirus E1a, SV40 large T Ag, and papillomavirus E7. These viral proteins bind and inactivate pRB, and the function of inactivating pRB is important in facilitating viral replication. The pRB protein interacts with the E2F transcription factor, which is involved in the expression of the adenovirus E2 gene and several cellular genes, and inhibits the activity of this transcription factor (Bagchi et al. (1991) Cell 65: 1063; Bandara et al. (1991) Nature 351: 494; Chellappan et al. (1992) Proc. Natl. Acad. Sci. (U.S.A.) 89: 4549.

The adenovirus, oncoproteins E1a, disrupts the pRB/E2F complex resulting in activation of E2F. However, neoplastic or normal dividing cells lacking sufficient functional pRB to complex E2F will not require the presence of a functional oncoprotein, such as E1a, to possess transcriptionally active E2F. Therefore, it is believed that replication deficient adenovirus species which lack the capacity to complex RB but substantially retain other essential replicative functions will exhibit a replication phenotype in cells which are deficient in RB function (e.g., normal dividing cells, or cells which are homozygous or heterozygous for substantially deleted RB alleles, cells which comprise RB alleles encoding mutant RB proteins which are essentially nonfunctional, cells which comprise mutations that result in a lack of function of an RB protein) but will not substantially exhibit a replicative phenotype in non-replicating, non-neoplastic cells. Such replication deficient adenovirus species are referred to as $E1a\text{-}RB^{(-)}$ replication deficient adenoviruses.

A cell population (such as a mixed cell culture or a human cancer patient) which comprises a subpopulation of neoplastic cells and dividing normal cells both lacking RB function, and a subpopulation of non-dividing, non-neoplastic cells which express essentially normal RB function can be contacted under infective conditions (i.e., conditions suitable for adenoviral infection of the cell population, typically physiological conditions) with a composition comprising an infectious dosage of a $E1a\text{-}RB^{(-)}$ replication deficient adenovirus. This results in an infection of the cell population with the $E1a\text{-}RB^{(-)}$ replication deficient adenovirus. The infection produces preferential expression of a replication phenotype in a significant fraction of the cells comprising the subpopulation of neoplastic and dividing normal cells lacking RB function ($RB^-$ cell) but does not produce a substantial expression of a replicative phenotype in the subpopulation of non-dividing neoplastic cells having essentially normal RB function. The expression of a replication phenotype in an infected $RB^{(-)}$ cell (neoplastic or dividing normal cells) results in the death of the cell, such as by cytopathic effect (CPE), cell lysis, apoptosis, and the like, resulting in a selective ablation of such $RB^{(-)}$ cells from the cell population. See, U.S. Pat. Nos. 5,801,029 and 5,972,706.

Typically, E1a-RB$^{(-)}$ replication deficient adenovirus constructs suitable for selective killing of RB(−) neoplastic cells comprise mutations (e.g., deletions, substitutions, frameshifts) which inactivate the ability of an E1a polypeptide to bind RB protein effectively. Such inactivating mutations typically occur in the E1a CR1 domain (amino acids 30-85 in Ad5: nucleotide positions 697-790) and/or the CR2 domain (amino acids 120-139 in Ad5; nucleotide positions 920-967), which are involved in binding the p105 RB protein and the p107 protein. Preferably, the CR3 domain (spanning amino acids 150-186) remains and is expressed as a truncated p289R polypeptide and is functional in transactivation of adenoviral early genes. FIG. 1 portrays schematically the domain structure of the E1a-289R polypeptide.

In addition to alterations in the E1 a region of adenovirus, it would be desirable to enhance viral specific killing of neoplastic cells that lack RB function by constructing viruses that have critical replicative functions under the control of transcriptionally active E2F. The adenovirus replication cycle has two phases: an early phase, during which 4 transcription units E1, E2, E3, and E4 are expressed, and a late phase which occurs after the onset of viral DNA synthesis when late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth. See, Halbert, D. N., et al., 1985, J Virol. 56:250-7.

If the adenoviral regions that are involved in virus replication could be brought under the control of E2F via an E2F responsive transcriptional unit, this would provide an enhanced adenovirus that selectively kills neoplastic cells that lack RB function, but not normal cells.

By way of background, the following references are presented relating to adenoviral vectors with alterations in regions involved in viral replication, including the E4 region, and E2F responsive promoters.

WO 98/091563, inventors Branton et al., presents methods and compositions for using adenoviral E4 proteins for inducing cell death.

Gao, G-P., et al., describe the use of adenoviral vectors with E1 and E4 deletions for liver-directed gene therapy. See, J. Virology, December 1996, p. 8934-8943.

WO 98/46779 describes certain adenoviral vectors capable of expressing a transgene comprising a modified E4 region but retaining E4orf3.

Yeh, P., et al describe the expression of a minimal E4 functional unit in 293 cells which permit efficient dual trans-complementation of adenoviral E1 and E4 regions. See, Yeh, P., et al J. Virology, January 1996, pages 559-565.

U.S. Pat. No. 5,885,833 describes nucleic acid constructs comprising an activator sequence, a promoter module, and a structural gene. The promoter module comprises a CHR region and a nucleic acid sequence that binds a protein of the E2F family.

Wang, Q. et al., in Gene Ther. 2:775-83 (1995) describe a 293 packaging cell line for propagation of recombinant adenovirus vectors that lack E1 and/or E4 regions. To avoid the transactivation effects of the E1A gene product in parental 293 cells as well as the over expression of the E4 genes, the E4 promoter was replaced by a cellular inducible hormone gene promoter, the mouse alpha inhibin promoter. Krougliak and Graham describe the development of cell lines that express adenovirus type 5 E1, E4, and pIX genes, and thus are able to complement replication of adenovirus mutants defective in each of these regions. See, Krougliak, V. and Graham, F., Human Gene Therapy, vol. 6: p. 1575-1586, 1995. Fang, B., et al. in J. Virol. 71:4798-803 (1997) describe an attenuated, replication incompetent, adenoviral vector that has the E4 promoter replaced with a synthetic GALA/VP16 promoter that facilitates packaging of the adenoviral vector in 293 cells that stably express the GAL4/VP16 transactivator. The virus was made replication incompetent by deletion of the E1 region of the virus.

U.S. Pat. No. 5,670,488 describes adenoviral vectors having one or more of the E4 open reading frames deleted, but retaining sufficient E4 sequences to promote virus replication in vitro, and having a DNA sequence of interest operably linked to expression control sequences and inserted into the adenoviral genome.

U.S. Pat. No. 5,882,877 describes adenoviral vectors having the E1, E2, E3 and E4 regions and late genes of the adenovirus genome deleted and additionally comprising a nucleic acid of interest operably linked to expression control sequences.

WO 98/13508 describes selectively targeting malignant cells using an E2F responsive promoter operably linked to a transgene of interest.

Neuman, E., et al., show that the transcription of the E2F-1 gene is rendered cell cycle dependent by E2F DNA-binding sites within its promoter. See, Mol Cell Biol. 15:4660 (1995). Neuman, E., et al also show the structure and partial genomic sequence of the human E2F1 gene. See, Gene. 173:163-9 (1996).

Parr, M. J., et al., show that tumor-selective transgene expression in vivo is mediated by an E2F-responsive adenoviral vector. See, Nat Med. 3:1145-9 (1996). Adams, P. D., and W. G. Kaelin, Jr. show transcriptional control by E2F. See, Semin Cancer Biol. 6:99-108 (1995).

Hallenbeck, P., et al., describe vectors for tissue-specific replication. One such vector is adenovirus that is stated to selectively replicate in a target tissue to provide a therapeutic benefit from the vector per se, or from heterologous gene products expressed from the vector. In the former instance a tissue-specific transcriptional regulatory sequence is operably linked to a coding region of a gene that is essential for replication of the vector. Several coding regions are described including E1a, E1B, E2 and E4. See, WO 96/17053 and WO 96/17053.

Henderson, et al., in U.S. Pat. No. 5,698,443 shows an adenovirus vector having at least one of the genes E1A, E1B or E4 under the transcriptional control of a prostate cell specific response element.

It should be apparent that viruses offer another means for treating cancer. Thus, viruses that selectively replicate in, and kill neoplastic cells would be an invaluable weapon in a physician's arsenal in the battle against cancer.

SUMMARY OF THE INVENTION

The invention described herein provides recombinant adenoviral vectors and methods and compositions for constructing the same, preferably replication competent, adenoviral vectors that substantially and selectively kill neoplastic cells with little or no killing of non neoplastic cells that have at least one, and preferably two, adenoviral promoter regions that control the expression of immediate early genes altered such that certain transcriptional nucleotide regulatory start sites are removed, or otherwise inactivated, while retaining those sites that are required, or that substantially facilitate viral replication, and substituting for the removal of such nucleotide regulatory start sites, a tumor cell specific transcriptional unit, and optionally, a heterologous gene with anti-neoplastic cell activity is substituted for a deleted viral gene.

The invention further provides recombinant viral vectors and methods as described above, wherein the adenoviral promoter regions are preferably the E1a and/or E4, and the heterologous gene is expressed late in the viral replication cycle, and which heterologous gene is under the control of adenoviral endogenous gene expression machinery.

In another aspect, the invention provides adenoviral vectors that substantially and selectively kill neoplastic cells with little or no killing of non neoplastic cells that have certain E1a and E4 promoter transcriptional nucleotide start sites removed, or otherwise inactivated, and substituting therefore a tumor cell specific transcriptional unit.

In another aspect, the invention provides adenoviral vectors that substantially and selectively kill neoplastic cells with little or no killing of non neoplastic cells that have at least certain of the E4 promoter transcriptional nucleotide start sites removed, or otherwise inactivated, while retaining those sites that facilitate viral replication, including certain of the Sp1, ATF, NF1 and NFIII/Oct-1 binding sites, and substituting for the E4 promoter nucleotide start sites a tumor cell specific transcriptional unit.

An object of the invention is a description of an adenoviral vector as described above having the E1a and/or the E4 promoter transcriptional nucleotide start sites removed and substituted therefore a tumor cell specific transcriptional unit wherein such adenoviral vectors further exhibit mutations (e.g., deletions, substitutions, frameshifts) which inactivate the ability of an E1a polypeptide to bind RB protein effectively.

A further feature of the invention consists of substituting for the E1a and/or E4 promoter nucleotide start sequences referred to above with a tumor cell specific transcriptional unit, one that is responsive to the pRb signaling pathway, including pRb/p107, E2F-1/-2/-3, G1 cyclin/cdk complexes, and preferably the promoter is E2F responsive.

The invention also presents methods for preventing or treating disease, and preferably disease resulting from hyperproliferative cell growth, including neoplastic disease using the adenoviral vectors described herein, alone or in combination with anti-neoplastic agents.

Yet another feature of the invention is a method for treating neoplastic disease using adenoviral vectors described above wherein the heterologous gene substituted for a deleted viral gene(s) is expressed late in the viral replication cycle to enhance the anti-neoplastic activity of the adenoviral vector.

The above aspects of the invention, as well as others not described above, will become apparent upon a full consideration of the invention.

DETAILED DESCRIPTION OF THE INVENTION

Figure 1:
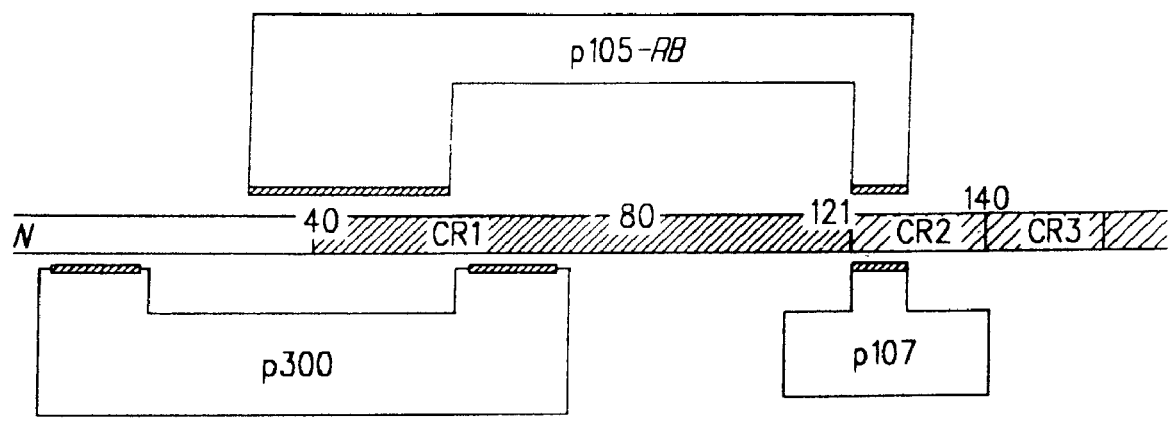
FIG. 1 portrays schematically the domain structure of the E1a-289R polypeptide.

All publications, including patents and patent applications, mentioned in this specification are herein incorporated by reference to the same extent as if each individual publication was specifically and individually indicated to be incorporated by reference in its entirety.

Furthermore, it is important to note that while the invention adenoviral vectors' oncolytic activity is ascribed to a mechanism of action involving molecules in the pRb pathway that affect the expression of viral genes under the control of an E2F responsive promoter, the invention should not be construed as limited by this mechanism. Rather it will be appreciated that the invention adenoviral vectors' oncolytic activity is a function of its structural elements which are thought to, but may not exert oncolysis through the pRb pathway. Thus, the invention adenoviral vectors derive their tumor versus normal cell killing selectivity by having at least one E2F responsive promoter driving either E1a or E4 gene expression. The preferred adenoviral vector is one having 2 E2F responsive promoters, one substituted for the E1a promoter and the other for the E4 promoter, as described below.

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al, Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

The phrase "endogenous gene expression machinery" refers to those endogenous viral elements responsible for gene expression including, by way of example, nucleotide sequences that comprise promoters, enhancers, alternative splicing sites, alternative translation initiation sites, polyadenylation signals, etc.

Those skilled in the art will also recognize publications that facilitate genetic engineering of the invention adenovirus to produce the invention E1A and/or E4 shuttle vectors. Such would include the work of Hitt, M., et al Construction and propagation of human adenovirus vectors. In: Cell Biology: a Laboratory Handbook; J. Celis (Ed), Academic Press, N.Y. (1996); Graham, F. L. and Prevec, L. Adenovirus based expression vectors and recombinant vaccines. In: Vaccines: New Approaches to Immunological Problems. R. W. Ellis (ed) Butterworth. Pp. 363-390; and Graham, F. L. and Prevec, L. Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109-128, 1991. The materials and methods described in these articles were or could be used below.

In the formulae representing selected specific embodiments of the present invention, the amino- and carboxy-terminal groups, although often not specifically shown, will be understood to be in the form they would assume at physiological pH values, unless otherwise specified. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid, in keeping with standard polypeptide nomenclature (described in J. Biol. Chem., 243:3552-59 (1969) and adopted at 37 CFR §1.822(b)(2)).

As employed throughout the disclosure, the following terms, unless otherwise indicated, shall be understood to have the following meanings:

The term "inactivated" as applied to "adenoviral transcriptional nucleotide regulatory site" sequences means rendering such sequences non functional by mutation, including by deletion of all or part of the sequences, or insertion of other sequences into the adenoviral transcriptional nucleotide sequences thereby rendering them non functional.

The term "adenovirus" as referred to herein indicates over 47 adenoviral subtypes isolated from humans, and as many from other mammals and birds. See, Strauss, "Adenovirus infections in humans," in The Adenoviruses, Ginsberg, ed., Plenum Press, New York, N.Y., pp. 451-596 (1984). The term preferably applies to two human serotypes, Ad2 and Ad5.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used.

By the phrase "tumor cell specific," as applied to the selectivity of killing of the invention adenoviruses, is meant tumor cells that are killed by the expression of viral genes operably linked to an E2F responsive promoter. Considering that E2F is expressed by normal cell, particularly dividing normal cells, it would be expected that the invention adenoviruses will also kill dividing normal cells, albeit, to a lesser degree than tumor cells.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence that is compared to some other sequence. Gaps (in either of the two sequences) are permitted to maximize matching; gap lengths of 15 bases or less are usually used, 6 bases or less are preferred with 2 bases or less more preferred.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as may be used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

It is important to note that while a preferred embodiment of the invention is the incorporation of the human E2F-1 promoter, a promoter that is "substantially identical" is intended to come within the definition of an E2F responsive promoter.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "polypeptide fragment" or "peptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically 8-10 amino acids long, preferably at least 10-20 amino acids long, and even more preferably 20-70 amino acids long.

By the phrase "pRB pathway," or "pRb signaling pathway" is meant, at least in part, molecules that affect pRb activity including pRb/p107, E2F-1/-2/-3, and G1 cyclin/cdk complexes. It will be appreciated that molecules not presently known may also come within this definition. These molecules mediate their biological effects, at least in part, at the level of transcription through an E2F responsive promoter.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference.

The production of proteins from cloned genes by genetic engineering is well known. See, e.g. U.S. Pat. No. 4,761,371 to Bell et al. at column 6, line 3 to column 9, line 65. The discussion which follows is accordingly intended as an overview of this field, and is not intended to reflect the full state of the art.

DNA which encodes proteins may be inserted into the E1A and/or E4 adenoviral constructs of the invention, in view of the instant disclosure, by chemical synthesis, by screening reverse transcripts of mRNA from appropriate cells or cell line cultures, by screening genomic libraries from appropriate cells, or by combinations of these procedures, as illustrated below. For example, one embodiment of the invention is the expression of genes that encode prodrug activity enzymes where such genes are incorporated into regions of the invention adenoviruses that do not affect their ability to replicate. Screening of mRNA or genomic DNA may be carried out with oligonucleotide probes generated from known gene sequence information. Probes may be labeled with a detectable group.

In the alternative, a gene sequence may be recovered by use of the polymerase chain reaction (PCR) procedure. See U.S. Pat. No. 4,683,195 to Mullis et al. and U.S. Pat. No. 4,683,202 to Mullis.

A vector is a replicable DNA construct, and is used either to amplify DNA encoding a desired protein and/or to express DNA which encodes the protein. An expression vector is a replicable DNA construct in which a DNA sequence encoding a protein of interest is operably linked to suitable control sequences capable of effecting the expression of the protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame. A preferred embodiment promoter of the instant invention in those instances where endogenous adenoviral E1a and/or E4 region promoter transcriptional nucleotide regulatory start sites are removed is the substitution with a tumor cell specific promoter, one that is responsive, directly or indirectly, to molecules in the pRb signaling pathway, including the proteins pRb/p107, E2F-1/-2/-3, G1 cyclin/cdk complexes, and preferably the promoter is E2F responsive, and more preferably the promoter is the human E2F-1.

By responsive to molecules in the pRb signaling pathway, is meant the killing of tumor cells caused by the expression of viral genes under the control an E2F responsive promoter. Suitable host cells for use in the invention include prokaryotes, yeast cells, or higher eukaryotic cells. Prokaryotes include gram negative or gram positive organisms, for example Escherichia coli (E. coli) or Bacilli. Higher eukaryotic cells include established cell lines of mammalian origin as described below. Exemplary host cells are DH5a, E. coli W3110 (ATCC No. 27,325), E. coli B, E. coli X1776 (ATCC No. 31,537) and E. coli 294 (ATCC No. 31,446).

Cultures of cells derived from multicellular organisms are a desirable host for recombinant protein synthesis. In principal, any higher eukaryotic cell culture is workable, whether from vertebrate or invertebrate culture. However, mammalian cells are preferred. Propagation of such cells in cell culture has become a routine procedure. See Tissue Culture, Academic Press, Kruse and Paterson, editors (1973). Examples of useful host cell lines are VERO and HeLa cells, Chinese hamster ovary (CHO) cell lines, and FL5.12, W1138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

As used herein, the term "replication deficient virus" refers to a virus that preferentially inhibits cell proliferation, causes cell lysis, or induces apoptosis (collectively considered killing) in a predetermined cell population (e.g., tumor cells responsive to molecules in the pRb signaling pathway) which supports expression of a virus replication phenotype, and which is substantially unable to inhibit cell proliferation, cause cell lysis, induce apoptosis, or express a replication phenotype in non-replicating, non-transformed cells.

The term "RB function" refers to the property of having an essentially normal level of a polypeptide encoded by the RB gene (i.e., relative to non-neoplastic cells of the same histological type), wherein the RB polypeptide is capable of binding an E1a protein of wild-type adenovirus 2 or 5. For example, RB function may be lost by production of an inactive (i.e., mutant) form of RB or by a substantial decrease or total loss of expression of pRB polypeptide(s), or by an alteration in one or more of the molecules in the pRb pathway that effect pRb levels. Alternatively, "RB function" refers to the normal transcriptional activity of genes, in terms of time of expression and amounts of proteins expressed, that are under the control of an E2F responsive, pRb pathway sensitive, promoter.

RB function may be substantially absent in neoplastic cells that comprise RB alleles encoding a wild-type RB protein; for example, a genetic alteration outside of the RB locus, such as a mutation that results in aberrant subcellular processing or localization of RB, or a molecule in the pRB pathway, may result in a loss of RB function.

The term "replication phenotype" refers to one or more of the following phenotypic characteristics of cells infected with a virus such as a replication deficient adenovirus: (1) substantial expression of late gene products, such as capsid proteins (e.g., adenoviral penton base polypeptide) or a heterologous gene that exhibits a late expression profile, or RNA transcripts initiated from viral late gene promoter(s), (2) replication of viral genomes or formation of replicative intermediates, (3) assembly of viral capsids or packaged virion particles, (4) appearance of cytopathic effect (CPE) in the infected cell, (5) completion of a viral lytic cycle, and (6) other phenotypic alterations which are typically contingent upon abrogation of RB function in non-neoplastic cells infected with a wild-type replication competent DNA virus encoding functional oncoprotein(s). A replication phenotype comprises at least one of the listed phenotypic characteristics, preferably more than one of the phenotypic characteristics.

The term "antineoplastic replication deficient virus" is used herein to refer to a recombinant virus which has the functional property of inhibiting development or progression of a neoplasm in a human, by preferential cell killing, whether by lysis or apoptosis of infected neoplastic cells relative to infected non-replicating, non-neoplastic cells of the same histological cell type.

As used herein, "neoplastic cells" and "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly-differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as tumor cells or cancer cells, typically termed carcinoma if originating from cells of endodermal or ectodermal histological origin, or sarcoma if originating from cell types derived from mesoderm.

As used herein, "physiological conditions" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl (or optionally KCl), pH 6.5-8.1, and a temperature of approximately 20-45° C. Generally, physiological conditions are suitable binding conditions for intermolecular association of biological macromolecules. For example, physiological conditions of 150 mM NaCl, pH 7.4, at 37° C. are generally suitable.

EMBODIMENTS OF THE INVENTION

The E1a and E4 regions of adenovirus are essential for an efficient and productive infection of human cells. The E1a gene is the first viral gene to be transcribed in a productive infection, and its transcription is not dependent on the action of any other viral gene products. However, the transcription of the remaining early viral genes requires E1a gene expression. The E1a promoter, in addition to regulating the expression of the E1a gene, also integrates signals for packaging of the viral genome as well as sites required for the initiation of viral DNA replication. See, Schmid, S. I., and Hearing, P. in Current Topics in Microbiology and Immunology, vol. 199: pages 67-80 (1995).

The invention as applied to E1a adenoviral vectors involves the replacement of the basic adenovirus E1a promoter, including the CAAT box, TATA box and start. site for transcription initiation, with a basic promoter that exhibits tumor specificity, and preferably is E2F responsive, and more preferably is the human E2F-1 promoter. Thus, this virus will be repressed in cells that lack molecules, or such molecules are non functional, that activate transcription from the E2F responsive promoter. Normal non dividing, or quiescent cells, fall in this class, as the transcription factor, E2F, is bound to pRb, or retinoblastoma protein, thus making E2F unavailable to bind to and activate the E2F responsive promoter. In contrast, cells that contain free E2F should support E2F based transcription. An example of such cells are neoplastic cells that lack pRb function, allowing for a productive viral infection to occur.

Retention of the enhancer sequences, packaging signals, and DNA replication start sites which lie in the E1a promoter will ensure that the adenovirus infection proceeds to wild type levels in the neoplastic cells that lack pRb function. In essence, the modified E1a promoter confers tumor specific transcriptional activation resulting in substantial tumor specific killing, yet provides for enhanced safety in normal cells.

Figure 2:
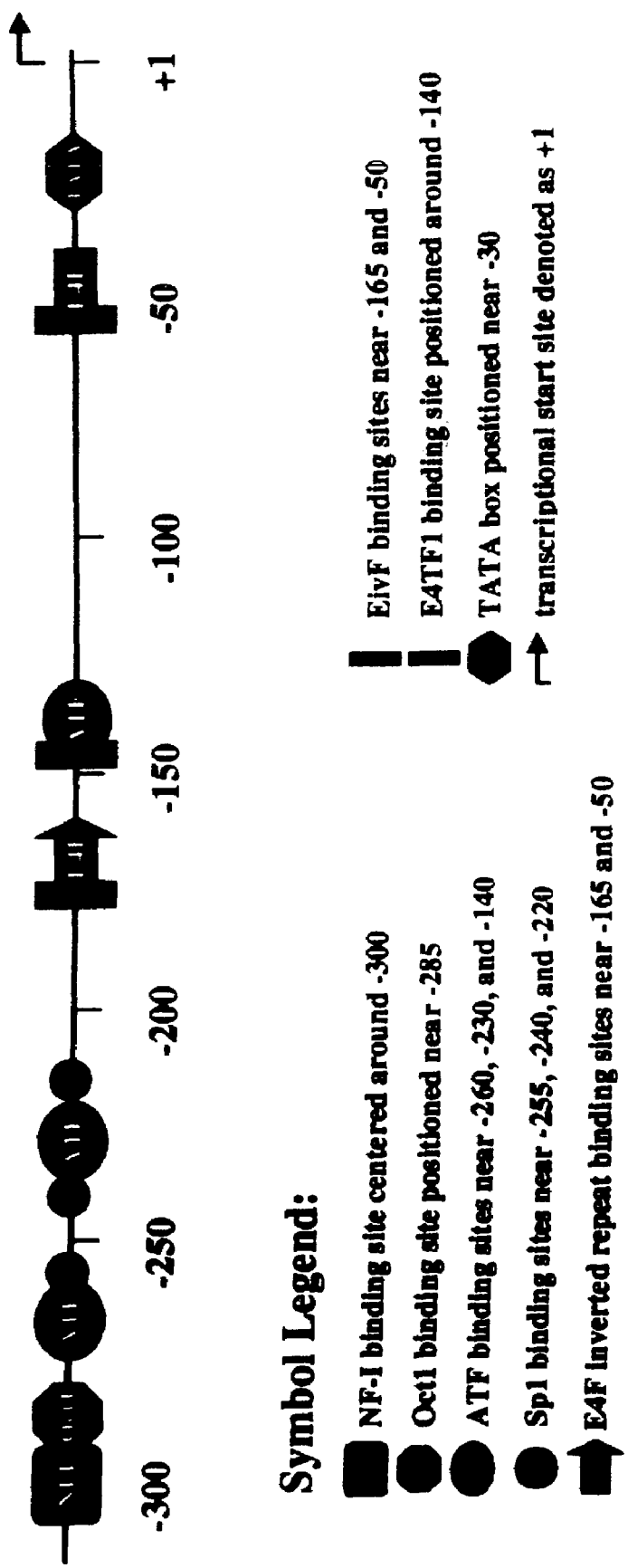
FIG. 2 shows the adenoviral E4 promoter.

In creating the E1a adenoviral vector by substituting the endogenous E1a promoter with the E2F responsive promoter, the elements upstream of nucleotide 375 in the adenoviral 5 genome are kept intact. The nucleotide numbering is as described by See, Schmid, S. I., and Hearing, P. Current Topics in Microbiology and Immunology, vol. 199: pages 67-80 (1995). This includes all of the seven A repeat motifs identified for packaging of the viral genome (See FIG. 2 of Schmid and Hearing, above.) Sequences from nucleotide 375 to nucleotide 536 are deleted by a BsaAI to BsrBI restriction start site, while still retaining 23 base pairs upstream of the translational initiation codon for the E1A protein. An E2F responsive promoter, preferably human E2F-1 is substituted for the deleted endogenous E1a promoter sequences using known materials and methods. The E2F-1 promoter may be isolated as described in Example 1.

Figure 3:
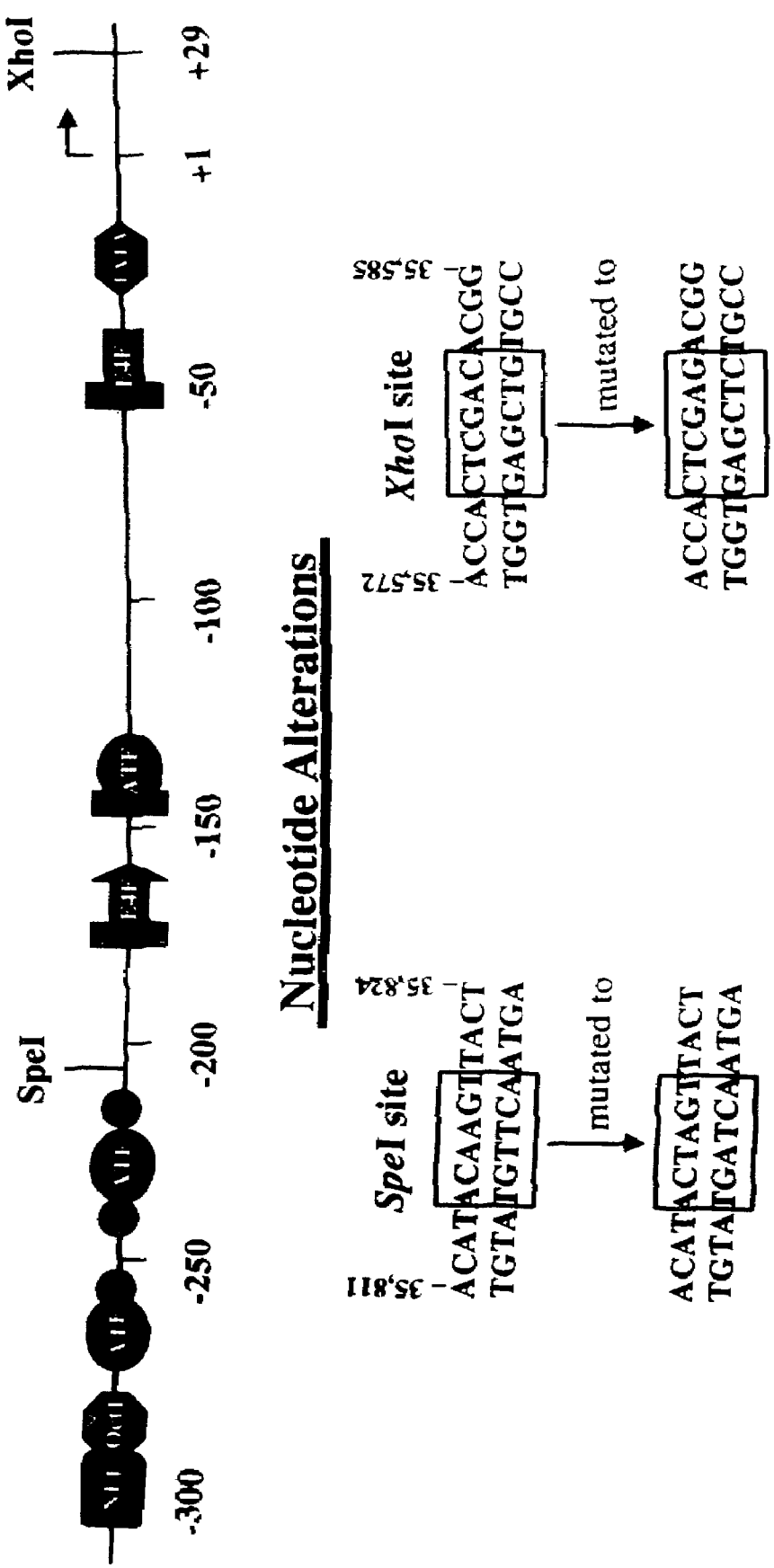
FIG. 3 shows diagrammatically the invention E4 shuttle vector and the position of the restriction sites, SpeI and XhoI, which facilitates substitution of the E4 promoter with a promoter of choice.

The E4 region has been implicated in many of the events that occur late in adenoviral infection, and is required for efficient viral DNA replication, late mRNA accumulation and protein synthesis, splicing, and the shutoff of host cell protein synthesis. Adenoviruses that are deficient for most of the E4 transcription unit are severely replication defective and, in general, must be propagated in E4 complementing cell lines to achieve high titers. The E4 promoter is positioned near the right end of the viral genome and governs the transcription of multiple open reading frames (ORF). A number of regulatory elements have been characterized in this promoter that are critical for mediating maximal transcriptional activity. In addition to these sequences, the E4 promoter region contains regulatory sequences that are required for viral DNA replication. A depiction of the E4 promoter and the position of these regulatory sequences can be seen in FIGS. 2 and 3.

Another embodiment of the invention is the generation of an adenoviral vector that has the E4 basic promoter substituted with one that has been demonstrated to show tumor specificity, preferably an E2F responsive promoter, and more preferably the human E2F-1 promoter. The reasons for preferring an E2F responsive promoter to drive E4 expression are the same as were discussed above in the context of an E1a adenoviral vector having the E1a promoter substituted with an E2F responsive promoter. The tumor suppressor function of pRb correlates with its ability to repress E2F-responsive promoters such as the E2F-1 promoter (Adams, P. D., and W. G. Kaelin, Jr. 1995, Cancer Biol. 6:99-108; Sellers, W. R., and W. G. Kaelin. 1996. published erratum appears in Biochim Biophys Acta 1996 Dec. 9;1288(3):E-1, Biochim Biophys Acta. 1288:M1-5. Sellers, W. R., J. W. Rodgers, and W. G. Kaelin, Jr. 1995, Proc Natl Acad Sci U S A. 92:11544-8.) The human E2F-1 promoter has been extensively characterized and shown to be responsive to the pRb signaling pathway, including pRb/p107, E2F-1/-2/-3, and G1 cyclin/cdk complexes, and E1A (Johnson, D. G., K. Ohtani, and J. R. Nevins. 1994, Genes Dev. 8:1514-25; Neuman, E., E. K. Flemington, W. R. Sellers, and W. G. Kaelin, Jr. 1995, Mol Cell Biol. 15:4660; Neuman, E., W. R. Sellers, J. A. McNeil, J. B. Lawrence, and W. G. Kaelin, Jr. 1996, Gene. 173:163-9.) Most, if not all, of this regulation has been attributed to the presence of multiple E2F sites present within the E2F-1 promoter. Hence, a virus carrying this (these) modification(s) would be expected to be attenuated in normal cells that contain an intact (wild type) pRb pathway, yet exhibit a normal infection/replication profile in cells that are deficient for pRb's repressive function. In order to maintain the normal infection/replication profile of this mutant virus we have retained the inverted terminal repeat (ITR) at the distal end of the E4 promoter as this contains all of the regulatory elements that are required for viral DNA replication (Hatfield, L. and P. Hearing. 1993, J Virol. 67:3931-9; Rawlins, D. R., P. J. Rosenfeld, R. J. Wides, M. D. Challberg, and T. J. Kelly, Jr. 1984, Cell. 37:309-19; Rosenfeld, P. J., E. A. O'Neill, R. J. Wides, and T. J. Kelly. 1987, Mol Cell Biol. 7:875-86; Wides, R. J., M. D. Challberg, D. R. Rawlins, and T. J. Kelly. 1987, Mol Cell Biol. 7:864-74.). This facilitates attaining wild type levels of virus in pRb pathway deficient tumor cells infected with this virus.

In the invention adenoviral constructs involving the E4 region, the E4 promoter is preferably positioned near the right end of the viral genome and it governs the transcription of multiple open reading frames (ORFs) (Freyer, G. A., Y. Katoh, and R. J. Roberts. 1984, Nucleic Acids Res. 12:3503-19; Tigges, M. A., and H. J. Raskas. 1984. Splice junctions in adenovirus 2 early region 4 mRNAs: multiple splice sites produce 18 to 24 RNAs. J Virol. 50:106-17; Virtanen, A., P. Gilardi, A. Naslund, J. M. LeMoullec, U. Pettersson, and M. Perricaudet. 1984, J Virol. 51:822-31.) A number of regulatory elements have been characterized in this promoter that mediate transcriptional activity (Berk, A. J. 1986, Annu Rev Genet. 20:45-79; Gilardi, P., and M. Perricaudet. 1986, Nucleic Acids Res. 14:9035-49; Gilardi, P., and M. Perricaudet. 1984, Nucleic Acids Res. 12:7877-88; Hanaka, S., T. Nishigaki, P. A. Sharp, and H. Handa. 1987, Mol Cell Biol. 7:2578-87; Jones, C., and K. A. Lee. 1991, Mol Cell Biol. 11:4297-305; Lee, K. A., and M. R. Green. 1987, Embo J. 6:1345-53.) In addition to these sequences, the E4 promoter region contains elements that are involved in viral DNA replication (Hatfield, L., and P. Hearing. 1993, J Virol. 67:3931-9; Rawlins, D. R., P. J. Rosenfeld, R. J. Wides, M. D. Challberg, and T. J. Kelly, Jr. 1984, Cell. 37:309-19; Rosenfeld, P. J., E. A. O'Neill, R. J. Wides, and T. J. Kelly. 1987, Mol Cell Biol. 7:875-86; Wides, R. J., M. D. Challberg, D. R. Rawlins, and T. J. Kelly. 1987, Mol Cell Biol. 7:864-74.) A depiction of the E4 promoter and the position of these regulatory sequences can be seen in FIGS. 1 and 2. See, also, Jones, C., and K. A. Lee. Mol Cell Biol. 11:4297-305 (1991). With these considerations in mind, an E4 promoter shuttle was designed by creating two novel restriction endonuclease sites: a XhoI site at nucleotide 35,576 and a SpeI site at nucleotide 35,815 (see FIG. 3). Digestion with both XhoI and SpeI removes nucleotides from 35,581 to 35,817. This effectively eliminates bases −208 to +29 relative to the E4 transcriptional start site, including all of the sequences that have been shown to have maximal influence on E4 transcription. In particular, this encompasses the two inverted repeats of E4F binding sites that have been demonstrated to have the most significant effect on promoter activation. However, all three Sp1 binding sites, two of the five ATF binding sites, and both of the NF1 and NFIII/Oct-1 binding sites that are critical for viral DNA replication are retained. Also, many of the E4 promoter elements that are removed can be substituted with sites that retain similar functions (e.g., transcriptional start site and the TATA box), yet now confer tumor cell specificity through the E2F responsive promoter sites.

The preferred E2F responsive promoter is the human E2F-1 promoter. Key regulatory elements in the E2F-1 promoter that mediate the response to the pRb pathway have been mapped both in vitro and in vivo (Johnson, D. G., K. Ohtani, and J. R. Nevins. 1994, Genes Dev. 8:1514-25; Neuman, E., E. K. Flemington, W. R. Sellers, and W. G. Kaelin, Jr. 1995, Mol Cell Biol. 15:4660; Parr, M. J., Y. Manome, T. Tanaka, P. Wen, D. W. Kufe, W. G. Kaelin, Jr., and H. A. Fine. 1997, *Nat Med.* 3:1145-9.) Thus, we isolated the human E2F-1 promoter fragment from base pairs −218 to +51, relative to the transcriptional start site, by PCR with primers that incorporated a SpeI and XhoI site into them. This creates the same sites present within the E4 promoter shuttle and allows for direct substitution of the E4 promoter with the E2F-1 promoter. The details of the construction of this vector are described more in the Examples.

One embodiment of the invention is the description of an adenovirus E1a and/or E4 shuttle vector that allows fast and easy substitution of the endogenous nucleotide transcriptional regulatory sequences, where such sequences are preferably E1a and/or E4 promoter sequences, with nucleotide transcriptional regulatory sequences that are response to elements (i.e. molecules) in the pRb signaling pathway, including pRb/p107, E2F transcription factors such as E2F-1/-2/-3, and G1 cyclin/cdk complexes. An E1a or E4 adenoviral vector, as described above, would be expected to be attenuated in normal cells that contain an intact, that is wild type pRb pathway, yet exhibit a normal infection profile in cells that are deficient in Rb pathway function, including for pRb's repressive function. Due to the presence of the autoregulatory E2F sites in the E2F-1 promoter, any E1A or E4 adenoviral vector having nucleotide transcriptional regulatory sequences that are response to elements in the pRb signaling pathway substituted for the endogenous E1a and/or E4 sequences will preferably have a second mutation in the E1A-CR2 (conserved region 2) domain. This is desirable to minimize E1A's ability to disrupt pRb-mediated repression of the E2F elements.

As referred to above, the adenoviral oncoprotein E1a, disrupts the pRB/E2F complex resulting in the release and thus the activation of E2F. The preferred E1a and/or E4 adenovirus shuttle vector construct is one that is mutant in those regions of E1a that bind to pRb and displace E2F. Thus, suitable E1a-RB replication deficient adenovirus constructs for use in the methods and compositions of the invention to generate the invention E1a and/or E4 shuttle vectors include, but are not limited to the following examples: (1) adenovirus serotype 5 NT dl 1010, which encodes an E1a protein lacking the CR1 and CR2 domains (deletion of amino acids 2 to 150; nucleotides 560-1009) necessary for efficient RB binding, but substantially retaining the CR3 domain (Whyte et al. (1989) Cell 56: 67), and (2) adenovirus serotype 5 dl 312, which comprises a deleted viral genome lacking the region spanning nucleotides 448-1349 which encodes the entire E1a region in wild-type adenovirus (Jones N and Shenk T (1979) Proc. Natl. Acad. Sci. (U.S.A.) 76: 3665). Ad5 NT dl 1010 is a preferred E1a-RB replication deficient adenovirus and is available from Dr. E. Harlow, Massachusetts General Hospital, Boston, Mass.).

Additional E1a mutants lacking the capacity to bind RB (E1 a$^{(-)}$ can be generated by those of skill in the art by generating mutations in the E1a gene region encoding E1a polypeptides, typically in the CR1 and/or CR2 domains, expressing the mutant E1a polypeptide, contacting the mutant E1 a polypeptides with p105 or a binding fragment of RB under aqueous binding conditions, and identifying mutant E1a polypeptides which do not specifically bind RB as being candidate E1a$^{(-)}$ mutants suitable for use in the invention. Alternative assays include contacting the mutant E1a polypeptides with the 300 kD protein and/or p107 protein or binding fragment thereof under aqueous binding conditions, and identifying mutant E1a polypeptides which do not specifically bind the 300 kD and/or p107 polypeptides as being candidate E1a$^{(-)}$ mutants suitable for use in the invention in the production of the E1a and/or E4 shuttle vectors. Alternative binding assays include determining the inability of E1a$^{(-)}$ mutant protein (or absence of E1a protein) to form complexes with the transcription factor E2F and/or to lack the ability to dissociate the RB protein from RB:E2F complexes under physiological conditions (Chellappan et al. 1991, Cell, June 14;65(6):1053-61).

Alternatively, functional assays for determining mutants lacking E1a function, such as loss of transctivation by E1a of transcription of various reporter polypeptides linked to a E1a-dependent transcriptional regulatory sequence, and the like, will be used. Such inactivating mutations typically occur in the E1a CR1 domain (amino acids 30-85 in Ad5: nucleotide positions 697-790) and/or the CR2 domain (amino acids 120-139 in Ad5; nucleotide positions 920-967), which are involved in binding the p105 RB protein and the p107 protein. Preferably, the CR3 domain (spanning amino acids 150-186) remains and is expressed as a truncated p289R polypeptide and is functional in transactivation of adenoviral early genes.

It is important to note that while the E2F responsive promoter human E2F-1 is the preferred promoter to replace the E1a and/or E4 endogenous promoters that any E2F responsive nucleotide sequence that is activated, directly or indirectly, by elements in the pRb pathway will adequately substitute for the endogenous promoters.

It is also important to note that while the construction of the E1a and/or E4 adenoviral vectors involves the removal of certain transcriptional nucleotide start sites that the exact number of such sites removed or retained should not be construed as limiting the invention. What is intended in describing the invention is that in the place of the endogenous promoters, the E2F responsive promoter functions to drive the E1a and/or E4 genes to kill tumor cells. This process will vary in degree depending on the number or type of transcriptional start sites that are present in the E2F responsive promoter.

As mentioned above, another aspect of the instant invention is the incorporation of heterologous genes into the invention adenoviral vectors. The adenovirus replication cycle has two phases: an early phase, during which 4 transcription units E1, E2, E3, and E4 are expressed, and a late phase which occurs after the onset of viral DNA synthesis when late transcripts are expressed primarily from the major late promoter (MLP). See, Halbert, D. N., et al., 1985, J Virol. 56:250-7. A desirable feature of the expression of a heterologous gene is that its expression occur late during the adenoviral replication cycle. Since the invention adenoviral vectors replicate in neoplastic cells where RB function is substantially absent, such heterologous genes are expressed in such neoplastic cells but not in normal cells. Thus, such adenoviral vectors with a heterologous gene have enhanced anti-neoplastic activity, in part attributed to the adenoviral vector replicating in the neoplastic cell, and in part attributed to the expression of the heterologous gene as a late function of adenoviral replication. Consequently, late expression of the heterologous gene is directly linked to neoplastic cell selectivity of adenoviral infection.

A surprising aspect of the invention adenoviral vectors is that heterologous genes inserted into the E3 region of the virus, preferably the E3B region, exhibit an expression pattern similar to genes expressed during the late phase of infection, that is, expression is dependent upon, or occurs during, viral DNA replication. Thus, while such viruses that have a heterologous gene inserted in the E3B region are the preferred embodiments for the expression of heterologous genes, it will be appreciated that late expression can also be realized by putting heterologous gene expression under the control of endogenous adenoviral gene expression machinery that regulates late gene expression, such as the major late promoter.

It is important to note that while the invention described herein is presented in terms of adenovirus and an E2F responsive promoter, that the invention is not limited to adenovirus. Indeed, the skilled practitioner of this art will recognize applications to virtually all viruses that exhibit a life cycle similar to adenovirus such that an E2F responsive promoter can be incorporated to control the expression of certain genes that confer on such viruses selective tumor cell killing.

Uses of the Invention

As mentioned above, the invention adenoviruses can be used to treat diseases which have altered pRb pathway function. Additionally, adenoviral therapy of the present invention may be combined with other antineoplastic protocols, such as conventional chemotherapy, or with other viruses. See U.S. Pat. No. 5,677,178. Chemotherapy may be administered by methods well known to the skilled practitioner, including systemically, direct injection into the cancer, or by localization at the site of the cancer by associating the desired chemotherapeutic agent with an appropriate slow release material or intra-arterial perfusing the tumor. The preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50-120 mg/m$^2$ over 3-6 hours. More preferably it is administered intravenously at a dose of 80 mg/m$^2$ over 4 hours. A second chemotherapeutic agent, which is preferably administered in combination with cisplatin is 5-fluorouracil. The preferred dose of 5-fluorouracil is 800-1200 mg/m$^2$ per day for 5 consecutive days.

Adenoviral therapy using the instant invention adenoviruses may be combined with other antineoplastic protocols, such as gene therapy. See, U.S. Pat. No. 5,648,478. As mentioned above, adenovirus constructs for use in the instant invention will exhibit specific cancer cell killing. Such constructs may also have prodrug activator genes, including thymidine kinase, cytosine deaminase, or others, that in the presence of the appropriate prodrug will enhance the antineoplastic effect of the invention E1a and/or E4 adenovirus vectors. See, U.S. Pat. No. 5,631,236.

Also, in the event that the instant invention adenoviral mutants elicit an immune response that dampens their effect in a host animal, they can be administered with an appropriate immunosuppressive drug to maximize their effect. Alternately, a variety of methods exist whereby the exterior protein coat of adenovirus can be modified to produce less immunogenic virus. See, PCT/US98/0503 where it is shown that a major immunogenic component of adenovirus' exterior coat, hexon protein, can be genetically engineered to be less immunogenic. This is done by creating a chimeric hexon protein by substituting for normal viral hexon protein epitopes a sequence of amino acids not normally found in hexon protein. Such adenoviral constructs are less immunogenic than the wild type virus.

Another aspect of the instant invention is the incorporation of heterologous genes with anti-neoplasia activity into the E1a and/or E4 shuttle vectors, preferably in the E1B, E3 regions of the virus, more preferably the E3B region, or in other regions of the virus where the heterologous gene exhibits a late expression pattern. Examples of such heterologous genes, or fragments thereof that encode biologically active peptides, include those that encode immunomodulatory proteins, and, as mentioned above, prodrug activators (i.e. cytosine deaminase, thymidine kinase, U.S. Pat. Nos. 5,358,866, and 5,677,178). Examples of the former would include interleukin 2, U.S. Pat. Nos. 4,738,927 or 5,641,665; interleukin 7, U.S. Pat. Nos. 4,965,195 or 5,328,988; and interleukin 12, U.S. Pat. No. 5,457,038; tumor necrosis factor alpha, U.S. Pat. Nos. 4,677,063 or 5,773,582; interferon gamma, U.S. Pat. Nos. 4,727,138 or 4,762,791; or GM-CSF, U.S. Pat. Nos. 5,393,870 or 5, 391,485. Additional immunomodulatory proteins further include macrophage inflammatory proteins, including MIP-3, (See, Well, T. N. and Peitsch, M C. J. Leukoc. Biol vol 61 (5): pages 545-50,1997), and cell suicide, or apoptosis inducing proteins, including BAD and BAX. See, Yang, E., et al. Cell, vol 80, pages 285-291 (1995); and Sandeep, R., et al Cell, vol. 91, pages 231-241 (1997). Monocyte chemotactic protein (MCP-3 alpha) may also be used. A preferred embodiment of a heterologous gene is a chimeric gene consisting of a gene that encodes a protein that traverses cell membranes, for example, VP22 or TAT, fused to a gene that encodes a protein that is preferably toxic to cancer but not normal cells. To increase the efficacy of the invention adenoviral E1A mutant constructs they may be modified to exhibit enhanced tropism for particular tumor cell types. For example, as shown in PCT/US98/04964 a protein on the exterior coat of adenovirus may be modified to display a chemical agent, preferably a polypeptide, that binds to a receptor present on tumor cells to a greater degree than normal cells. Also see, U.S. Pat. Nos. 5,770,442 and 5,712,136. The polypeptide can be antibody, and preferably is single chain antibody.

Purification of Adenoviral Mutants

Adenovirus is routinely purified by a number of techniques including cesium chloride banding using an ultracentrifuge. However, for large scale production of adenovirus, methods which give larger yields than those readily obtainable by cesium chloride ultracentrifugation are desirable, and involve one or more chromatographic steps. The preferred method utilizes ion exchange chromatography. See, for example, PCT/US97/21504; and Huyghe et al., Human Gene Therapy, vol. 6: 1403-1416 (1996).

Formulation

Adenovirus, including adenoviral mutants, may be formulated for therapeutic and diagnostic administration to a patient. For therapeutic or prophylactic uses, a sterile composition containing a pharmacologically effective dosage of adenovirus is administered to a human patient or veterinary non-human patient for treatment, for example, of a neoplastic condition. Generally, the composition will comprise about $10^3$ to $10^{15}$ or more adenovirus particles in an aqueous suspension. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral vector. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Adenoviruses of the invention, or the DNA contained therein, may also be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. Nos. 5,043,164, 4,957,735, 4,925,661; Connor and Huang (1985) J. Cell Biol. 101: 582; Lasic D D (1992) Nature 355: 279; Novel Drug Delivery (eds. Prescott L F and Nimmo W S: Wiley, New York, 1989); Reddy et al. (1992) J. Immunol. 148: page 1585). Immunoliposomes comprising an antibody that binds specifically to a cancer cell antigen (e.g., CALLA, CEA) present on the cancer cells of the individual may be used to target virions, or virion DNA to those cells.

The compositions containing the present adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the invention adenoviruses, or cocktails thereof, are administered to a patient not presently in a neoplastic disease state to enhance the patient's resistance to recurrence of a cancer or to prolong remission time. Such an amount is defined to be a "prophylactically effective dose." In this use, the precise amounts again depend upon the patient's state of health and general level of immunity.

The Examples which follow are illustrative of specific embodiments of the invention, and various uses thereof. They are set forth for explanatory purposes only, and are not to be taken as limiting the invention.

EXAMPLES

Example 1

E2F-1E4 Adenoviral Vector Construction

The recombinant plasmid pAd75-100 was obtained from Patrick Hearing and contains the Ad5 dl309 fragment from the EcoRI site at 75.9 map units (m.u.) to the right end of the viral genome at 100 m.u. (a BamHI linker is located at 100 m.u.) in pBR322 between the EcoRI and BamHI sites. This EcoRI to BamHI fragment was directly subcloned into Litmus 28 (New England Biolabs) to generate L28:p75-100.dl309. The wild type Ad5 E3 sequence that is missing in dl309 (Ad5 nucleotides 30,005 to 30,750) was restored by replacing the NotI to NdeI fragment in L28:p75-100.dl309 with a wild type NotI to NdeI fragment (Ad5 nucleotides 29,510-31,089) from pAd5-SN (described in U.S. patent Ser. No. 09/347,604 unpublished in-house vector). This plasmid was designated L28:p75-100.wt. In order to generate the promoter shuttle, a slightly smaller vector was generated to be the mutagenesis template. Plasmid pKSII+:p94-100 was constructed by directly subcloning the EcoRV to BamHI fragment (Ad5 nucleotides 33,758 to 33,939) from pAD75-100 into pKSII+. A XhoI site at nucleotide 35,577 and a SpeI site at nucleotide 35,816 were created using the Stratagene Quickchange site directed mutagenesis method. The oligonucleotides used to generate these sites were: XhoI (5'-GCTGGTGCCGTCTCGAGTGGTGTTTTTTAATAGG-3' and its complement 5'-CCTATTAAAAAAACACCACTCGAGACG-GCACCAGC-3') and SpeI (5'-GGGCGGAGTAACTAG-TATGTGTTGGG-3' and its complement 5' CCCAACACAT-ACTAGTTACTCCGCCC-3'). This vector containing both the SpeI and XhoI restriction sites was designated pKSII+:E4PSV. Due to the presence of both a SpeI and XhoI site in the pKSII+ backbone, the EcoRV to BamHI fragment from pKSII+:E4PSV was subcloned into pRSET (Invitrogen) via the PvuII and BamHI sites and was designated as pRSET:E4PSV. All vectors and point mutations were verified by double stranded sequence analysis on an ABI automated sequencer.

The human E2F-1 promoter was isolated by the polymerase chain reaction (PCR) from templates pGL3:E2F-1(−242) and pGL3:E2F-1ΔE2F(−242). pGL3:E2F-1(−242) contains a wild type human E2F-1 promoter out to position −242 relative to the transcriptional start site. pGL3:E2F-1ΔE2F(−242) contains the same sequences except that both of the E2F binding-site palindromes contain inactivating point mutations. The primers used for PCR were as follows: SpeI-E2F1P (5'-GTGAGCACTAGTCGCCTGGTACCATCCG-GACAAAGCC-3') and XhoI-E2F1P (5'-GTGAGCCTC-GAGCTCGATCCCGCTCCGCCCCCGG-3'). One hundred nanograms of template DNA were PCR amplified using Pfu DNA polymerase (Stratagene) under the following conditions: an initial denaturation at 98° C. for 5 min., followed by 30 cycles of denaturation at 98° C. for 1 min. and annealing/primer extension at 68° C. for 1 min., followed by a final primer extension at 68° for 5 min. The PCR products were Qiagen purified, digested with SpeI and XhoI, gel purified, and ligated into SpeI and XhoI digested pRSET:E4PSV. These promoter shuttle vectors were designated E2F1-E4PSV and E2F1Δ-E4PSV and carry sequences from −218 to +51 relative to the transcriptional start of the human E2F1 promoter. The final vectors used to generate functional virus were created by subcloning the BstEII to BamHI fragments from both E2F1-E4PSV and E2F1Δ-E4PSV into both L28:p75-100.dl309 and L28:p75-100.wt digested with same enzymes. These vectors were designated as: E2F1-E4PSV.309, E2F1-E4PSV.wt, E2F1Δ-E4PSV.309, and E2F1Δ-E4PSV.wt. All vectors were confirmed by double stranded sequence analysis as described above.

Example 2

E2F1-E4 Adenovirus Construction

Ten micro grams of E2F1-E4PSV.309 were digested with EcoRI and BamHI, treated with calf-intestinal phosphatase, and gel purified. One micro gram of EcoRI digested dl922/47 TP-DNA was ligated to ~5 micro grams of the purified fragment containing the wild type E2F-1 promoter driving the E4 region overnight at 16° C. Ligations were transfected into 293 cells using standard a $CaPO_4$ transfection method. Briefly, the ligated DNA was mixed with 24 micro grams of salmon sperm DNA, 50 micro liters of 2.5M $CaCl_2$, and adjusted to a final volume of 500 micro liters with $H_2O$. This solution was added dropwise to 500 micro liters of Hepes-buffered saline solution, pH 7.05. After standing for 25 minutes, the precipitate was added dropwise to two 60 mm dishes of 293 cells which had been grown in DMEM supplemented with 10% fetal bovine serum (FBS) to 60-80% confluency. After 16 hours, the monolayer was washed one time with phosphate-buffered saline (minus calcium and magnesium) followed by a 5 ml agar overlay consisting of 1% Seaplaque agarose in DMEM supplemented with 2% FBS. Dishes were overlaid with 3-4 ml of the above agar overlay every 3-4 days until plaques were isolated.

Example 3

E2F1-E4 Viral Propagation and Confirmation

Primary plaques were isolated with a pasteur pipette and propagated in a 6 well dish on 293 cells in 2 ml of DMEM supplemented with 2% FBS until the cytopathic effect (CPE) was complete. One-tenth (200 ml) of the viral supernatant was set aside for DNA analysis, while the remainder was stored at −80° C. in a cryovial. DNA was isolated using Qiagen's Blood Kit as per their recommendation. One-tenth of this material was screened by PCR for the presence of the desired mutations using the following primers: for dl922/47 (5'-GCTAGGATCCGAAGGGATTGACTTACTCACT-3' and 5'-GCTAGAATTCCTCTTCATCCTCGTCGTCACT-3') and for the E2F-1 promoter in the E4 region (5'-GGTGACGTAGGTTTTAGGGC-3' and 5'-GCCATAACAGTCAGCCTTACC-3'). PCR was performed using Clontech's Advantage cDNA PCR kit in a Perkin Elmer 9600 machine using the following conditions: an initial denaturation at 98° C. for 5 min., followed by 30 cycles of denaturation at 98° C. for 1 min. and annealing/primer extension at 68° C. for 3 min., followed by a final primer extension at 68° for 5 min. Positive plaques (as determined by PCR) were subsequently verified by sequence analysis. The above PCR products were gel purified and sequenced with the same primers. Positive plaques were then subjected to a second round of plaque purification and verified as before. Viruses were propagated in 293 cells and purified by two rounds of cesium chloride gradient ultracentrifugation

Example 4

E2F1-E1a and E2F1-E1a/E2F1-E4 Vector Construction

The human E2F-1 promoter was isolated by the polymerase chain reaction (PCR) from templates pGL3:E2F-1(−242) and pGL3:E2F-1ΔE2F(−242). pGL3:E2F-1(−242) contains a wild type human E2F1 promoter out to position −242 relative to the transcriptional start site. pGL3:E2F-1ΔE2F(−242) contains the same sequences except that both of the E2F binding-site palindromes contain inactivating point mutations. The primers used for PCR were as follows: BamHI-E2F1P (5'-GTGAGCGGATCCGCTCGATCCCGCTCCGCCCCGG-3') and HindIII-E2F1P (5'-GTGAGCAAGCTTCGCCTGGTACCATCCGGACAAAGCC-3'). One hundred nanograms of template DNA were PCR amplified using Pfu DNA polymerase (Stratagene) under the following conditions: an initial denaturation at 98° C. for 5 min., followed by 30 cycles of denaturation at 98° C. for 1 min. and annealing/primer extension at 68° C. for 1 min., followed by a final primer extension at 68° for 5 min. The PCR products were purified over Qiaquick columns (Qiagen), digested with BamHI and HindIII, gel purified, and ligated into BamHI and HindIII partially digested p922/47-SV (see below). These promoter shuttle vectors were designated E2F1wt-922/47.PSV and E2F1Δ-922/47.PSV and carry sequences from −218 to +51 relative to the transcriptional start of the human E2F1 promoter. All vectors were confirmed by double stranded sequence analysis on an ABI automated sequencer.

P922/47-SV is an E1A promoter shuttle vector that also contains an E1A-CR2 deletion from nucleotides 922 to 947. Plasmid P922/47-SV was constructed by first digesting pSP64 (Promega) with HindIII, blunting with Klenow DNA polymerase, and then religating to generate pSP64 Delta H3. The 1,737 bp EcoRI to XbaI fragment (containing both Ad5 and pBR322 DNA) from pXC1 (Microbix) was then ligated into EcoRI and XbaI digested pSP64 Delta H3 to generate pSP64-RI/Xba. pSP64-RI/Xba was then digested with HindIII and BamHI, blunted with Klenow DNA polymerase and religated to generate P Delta E1 Delta +. This intramolecular deletion removed sequences from 9529 to 9875 of the pXC1 plasmid, effectively removing the HindIII, BamHI and ClaI sites. A novel HindIII site at nucleotide 376 of Ad5 was then created by digesting P Delta E1 Delta with BsAaI and ligating in a HindIII linker (NEB) to generate P Delta E1 Delta +H. A novel BamHI site was then created at nucleotide 539 of Ad5 by PCR mutagenesis. Two initial PCR reactions were performed. P Delta E1 Delta +H was used as a template with a primer 5'EcoXC1 site present in pBR322 and 3'Bam (5'-CGCGGAATTCTTTTGGATTGAAGCCAATATG-3') and 3'Bam (5'-CAGTCCCGGTGTCGGATCCGCTCGGAGGAG-3'), whereas plasmid pXC1 (Microbix) was used as the template in a PCR reaction with primers Bsr-Bam (5'-CTCCTCCGAGCGGATCCGACACCGGGACTG-3') and 3'E1A.Xba (5'-GCGGGACCACCGGGTGTATCTCAGGAGGTG-3'). The PCR products were isolated on an agarose gel and purified using a Qiagen gel extraction kit. The two PCR products were then mixed and PCR was repeated using the external most primers 5'EcoXC1 and 3'E1A.Xba. The resulting ~1,400 bp PCR product was then digested with EcoRI and XbaI and ligated into EcoRI and XbaI digested P Delta E1 Delta +H to generate Delta E1 Delta +H+B. pXC1-SV was then constructed by digesting P Delta E1 Delta +H+B with EcoRI and XbaI and ligating the 1,393 bp fragment into EcoRI and XbaI digested pXC 1 (Microbix). Finally, p922/47-SV was generated by using pCIA-922/47 (provided by Peter White) as a template for PCR with the following primers: Bsr-Bam (5'-CTCCTCCGAGCGGATCCGACACCGGGACTG-3') and 3'E1A.Xba (5'-GCATTCTCTAGACACAGGTG-3'). The resulting PCR product was purified over a Qiagen Qiaquick column, digested with BamHI and XbaI and subsequently ligated into pXC1-SV that had been digested with BamHI and XbaI.

Example 5

E2F1-E1a and E2F1-E1a/E2F1-E4 Viral Construction

ONYX-150 (E2F1wt-922/47) and ONYX-151 (E2F1 Delta-922/47) were generated by cotransfecting 10 micro grams of either E2F1wt-922/47.PSV or E2F1 Delta-922/47.PSV, respectively, with 10 micro grams of pJM17 (Microbix) into 293 cells using a standard $CaPO_4$ transfection method. ONYX-411 (E2F1wt-922/47 +E2F1wt-E4) was generated by digesting 10 micro grams of plasmid E2F1-E4PSV.309 (ID-086) with EcoRI and BamHI. The digested DNA was then treated with calf-intestinal phosphatase and gel purified. One microgram of EcoRI digested ONYX-150 (E2F1wt-922/47) TP-DNA was then ligated to 5 micro grams of the purified fragment containing the wild type E2F-1 promoter driving the E4 region overnight at 16° C. $CaPO_4$ transfections were performed by mixing the DNA's with 50 micro liters of 2.5M $CaCl_2$ in a final volume of 500 micro liters. In the case of ONYX-411, the transfection mix contained 24 micrograms of salmon sperm DNA in addition to the ligated DNA's. This solution was added dropwise to 500 micro liters of Hepes-buffered saline solution, pH 7.05. After standing for 25 minutes, the precipitate was added dropwise to two 60 mm dishes of 293 cells which had been grown in DMEM supplemented with 10% fetal bovine serum (FBS) to 60-80% confluency. After 16 hours, the monolayer was washed one time with phosphate-buffered saline (minus calcium and magnesium) followed by a 5 ml agar overlay consisting of 1% Seaplaque agarose in DMEM supplemented with 2% FBS. Dishes were overlaid with 3-4 ml of the above agar overlay every 3-4 days until plaques were isolated.

Example 6

E2F1-E1a and E2F1-E1a/E2F1-E4 Viral Propagation and Confirmation

Primary plaques were isolated with a pasteur pipette and propagated in a 6 well dish on either 293 or A549 cells in 2 ml of DMEM supplemented with 2% FBS until the cytopathic effect (CPE) was complete. One-tenth (200 micro liters) of the viral supernatant was set aside for DNA analysis, while the remainder was stored at −80° C. in a cryovial. DNA was isolated using Qiagen's Blood Kit as per their recommendation. One-tenth of this material was screened by PCR for the presence of the desired mutations using the following sets of primer pairs. The presence of the human E2F1 promoter driving E1A was confirmed using primers Ad5-left (5'-GGGCGTAACCGAGTAAGATTTGGCC-3') and E1Astart.NC (5'-GGCAGATAATATGTCT-CATTTTCAGTCCCGG-3'). The presence of the deletion from nucleotides 922 to 947 within E1A was verified using primers Af-7 (5-GCTAGGATCCGAAGGGATTGACT-TACTCACT-3') and Af-5 (5'-GCTAGAATTCCTCT-TCATCCTCGTCGTCACT-3'). The presence of the human E2F1 promoter driving the entire E4 region was confirmed using primers E4.3NCb (5'-GCCATAACAGTCAGCCT-TACC-3') and Ad5-3'end (5'-GGTGACGTAGGTTT-TAGGGC-3'). The deletion present in the E3 region (dl309) was confirmed using primers E3.C8 (5'-CCTTTATCCAGT-GCATTGACTGGG-3') and 3'-E3I (5'-GGAGAAAGTTTG-CAGCCAGG-3'). PCR was performed using Clontech's Advantage cDNA PCR kit in a Perkin Elmer 9600 machine using the following conditions: an initial denaturation at 98° C. for 5 min., followed by 30 cycles of denaturation at 98° C. for 1 min. and annealing/primer extension at 68° C. for 3 min., followed by a final primer extension at 68° for 5 min. Positive plaques (as determined by PCR analysis) were subsequently verified by sequence analysis. The above PCR products were gel purified and sequenced with the same primers. Positive plaques were then subjected to a second round of plaque purification in either 293 or A549 cells and verified exactly as before. Viruses were propagated in 293 cells and purified by two rounds of cesium chloride gradient ultracentrifugation. All large-scale viral preps were confirmed by the above same PCR and sequence analyses. In addition, all large-scale viral preps were verified by digestion with either HindIII or XhoI and the fragments analyzed by isolation on a 0.9% agarose gel.

Example 7

Construction of Onyx-443

Figure 4:
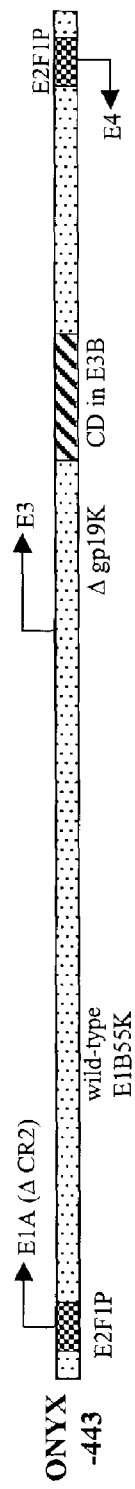
FIG. 4 shows (A) Genomic structure of ONYX-443. ONYX-443 has the CD gene inserted into the E3B region of ONYX-411. ONYX-443 also contains a complete deletion of gp19K. (B) in vitro CD expression in cells infected with ONYX-443. Human cancer cell lines and cultured normal human hepatocytes were infected at an MOI of 1 pfu/cell. At indicated time points, cell extracts were prepared and CD protein levels were analyzed by immunoblotting analysis.
Figure 4:
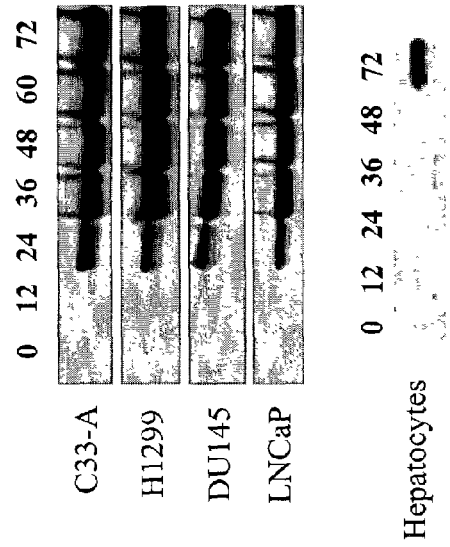

FIG. 4(A) shows the genomic structure of ONYX-443. It was constructed as follows. Plasmid pE3SV+V+B, described in U.S. patent application Ser. No. 09/347,604, was used to construct ONYX-443. This plasmid contains the E3 region of adenovirus. First, the 6.7K and gp19K genes from the E3 region were deleted by digesting pE3SV+V+B with NheI (28532) and natural MunI (29355) endonucleases, filled in using T4 DNA polymerase, and religated to create pE3SV+V+BΔgp 19K plasmid. The NheI and MunI sites were previously engineered into pE3SV+V+B.

Next, the *E. coli* cytosine deaminase gene (CD) (pCD2, ATCC No. 40999, Bethesda, Md., USA) was PCR amplified using primers CD-Cla (5'-CCCCCCAAGCTTATCGATAT-GTCGAATAAC-3') and CD-Swa (5'-TCCCCCGGGATT-TAAATTCGTTCAACGTTT-3'). The PCR product was purified and digested with ClaI and SwaI endonucleases and ligated with pE3SV+V+BΔgp19K, which was also digested with ClaI and SwaI to create. E3SV+V+BΔgp19K+CD(C/S). Note that the bacterial start codon of CD, GTG, was replaced with the eukaryotic start codon, ATG, in the primer design.

To facilitate homologous recombination with viral DNA, additional adenovirus sequences were added at the 5' region of pE3SV+V+BΔgp19K+CD(C/S). The plasmid was digested with SpeI and ligated with the 7533 bp fragment isolated from pNB following digestion with NheI (19549) and SpeI (27082) endonucleases to generate pNBΔgp19K-CD(C/S). pNB is described in U.S. patent application Ser. No. 09/347,604. Orientation of inserted DNA was confirmed by restriction digest since NheI and SpeI are compatible cohesive ends.

Lastly, Onyx-443 was produced by homologous recombination using viral TP-DNA from ONYX-411, which was digested with EcoRI (Hermiston T W, et al. In: Wold W S M (ed.). *Adenovirus Methods and Protocols*. Humana Press: Totowa, N.J., 1999, pp 11-24). Next, pNBΔgp19K-CD(C/S) was digested with BamHI, and the digested plasmid and TP-DNA were co-transfected in A549 cells using Lipofectamine as described by the manufacturer (Life Technologies), and recombinant virus, ONYX-443 was triple plaque purified and confirmed by PCR-sequencing using methods described previously (Hawkins L K et al. *Gene Therapy* 2001; 8: 1123-1131). Viral DNA from CsCl purified ONYX-443 viruses was confirmed by PCR analysis and DNA sequencing of the entire E1 and E3 region in addition of the E4 region for ONYX-443.

Example 8

Expression of Cytosine Deaminase in Onyx-443

The expression of CD in Onyx 443 was shown to occur both in vitro and in vivo.

In Vitro CD Expression. We first compared CD expression in cultured tumor cells (C33A, H1299, DU145 and LNCap) and primary normal human cells (human hepatocytes, quiescent small airway epithelial cells and mammary epithelial cells) following infection with ONYX-443 {(FIG. 4(B)}. At an MOI of 1, cancer cells infected with ONYX-443 expressed readily detectable levels of CD at 24 hours post infection. The amount of CD protein increased with time, reaching a maximum level at 72 hours post infection.

In contrast to cancer cells, normal cells infected with ONYX-443 did not express detectable levels of CD until 72 hours post infection, and the expression levels were significantly lower than in cancer cells. Similar results were obtained from quiescent as well as proliferative normal human small airway epithelial cells and mammary epithelial cells. The CD expression pattern following ONYX-443 infection was consistent with the differential replication of the parental ONYX-411 virus in tumor cells and normal cells. The CD expressed in these experiments was functional, capable of converting 5-FC to 5-FU in vitro.

Briefly, immunoblotting was performed as follows. Cultured cells were infected with at an MOI of 1. At indicated times post-infection, the cells were lysed in 100 mM Tris-Cl [pH 6.8], 5 mM EDTA, 1% SDS, 5% β-mercaptoethanol. For the animal studies, tumor samples were flash frozen and powderized in liquid nitrogen, and subsequently dissolved in the same lysis buffer. Cells debris was removed by centrifugation, and soluble proteins were fractionated by electrophoresis on (12%) pre-cast protein gels (BioWhitaker). After electrophoresis, the proteins were electrophoretically transferred to PVDF membranes. Blots were then incubated with antibodies diluted in PBS containing 1% dry milk and 0.1% Tween-20, and visualized by ECL (Amersham). Anti-CD antibody was diluted 1:50,000 [Hawkins, L. K., et al. Gene Ther, 8: 1123-1131, 2001. Rabbit anti-fiber antibody (American Qualex) was diluted 1:1000.

In Vivo CD Expression Following Intravenous Virus Administration. Next we injected ONYX-443 intravenously through tail vein into nude mice carrying human tumor xenografts, and examined CD activity in xenograft tumors and in normal tissues such as liver, lung and spleen. Briefly, tumors were established in nude mice through subcutaneous injection of $2 \times 10^6$ tumor cells. When tumors reached an average size of 100 mm$^3$, viruses were administrated intravenously through tail vein injection. Five consecutive daily injections were given to each animal at a dose of $2 \times 10^8$ pfu per day, with the exception of the DU145 study, in which ONYX-443 was dosed at $5 \times 10^8$ pfu per day for 5 consecutive days. The first day of virus administration was defined as Day 1. Animals were sacrificed at indicated time points and their tumor and normal tissue samples were analyzed for CD activity using a cytosine to uracil conversion assay.

Briefly, the CD assay was conducted as follows. Tumor and liver samples were flash frozen and powderized in liquid nitrogen. Twenty to forty milligrams of the tissue powder was lysed in 20 mM Tris-Cl, pH 8.0, 0.15 M NaCl, and 1% Triton X-100, and subsequently frozen and thawed for three times. For cytosine and 5-FC conversion assays, 200 μg of protein extract was incubated with [2-$^{14}$C] cytosine or [2-$^{14}$C] 5-fluorocytosine (1 μCi/mmol; Moravek Biochemicals, Brea, Calif.). The reactions were typically incubated for 2 hours at 37° C. Reaction products were separated on thin layer chromatography plates (VWR) and visualized by autoradiography.

Figure 5:
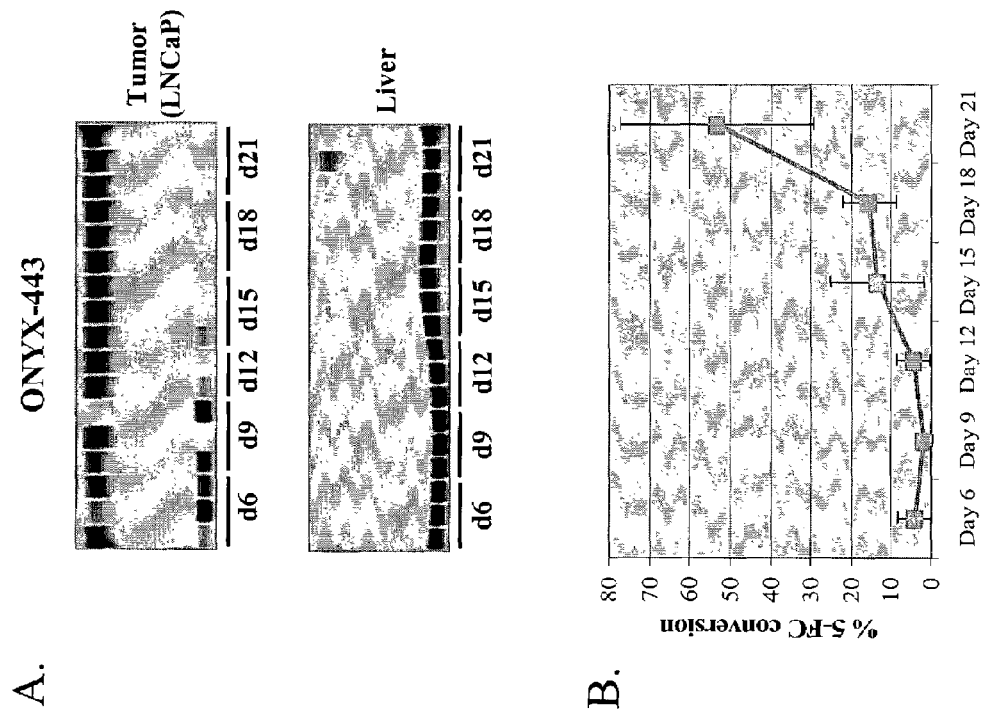
FIG. 5 shows CD expression in LNCaP xenograft tumors and liver following intravenous injection of ONYX-443. (A). Virus were administrated intravenously through tail vein injection into nude mice bearing LNCaP xenograft tumors. Five consecutive daily injections were given to each animal at a dose of $2 \times 10^8$ pfu per day. At indicated time points (in days, d), animals were sacrificed, tumors and livers were removed and analyzed for CD enzymatic activity using a $^{14}$C-cytosine-to-uracil conversion assay. The first day of virus administration was defined as Day 1. C: $^{14}$C-cytosine, U: $^{14}$C-uracil. Each lane represents an individual animal. Top panels: CD activity in LNCaP xenograft tumors. Bottom panels: CD activity in the corresponding mouse livers. 50 μg of total protein was used in each reaction. (B). CD activity was quantified using an assay that converts $^{14}$C-5-fluorocytosine (5-FC) to 5-fluorouracil (5-FU). The amount of 5-FC and 5-FU was determined using a PhosphoImager, and percentage of the input 5-FC that was converted to 5-FU was plotted.

Data from the LNCap xenograft model are shown in FIG. 5A. Two observations were made from this study. First, CD activity within tumors is high in animals injected with ONYX-443, and prolonged over time. Indeed, in animals injected with ONYX-443, tumor CD activity increased steadily throughout the entire study. This result is clearly demonstrated in FIG. 5B, where 5-FC was used as a substrate and the assay was done within the linear range. Second, CD activity in the liver of animals injected with ONYX-443 is low (FIG. 5A). In the vast majority of animals that received ONYX-443, no liver CD activity was detected.

Figure 6:
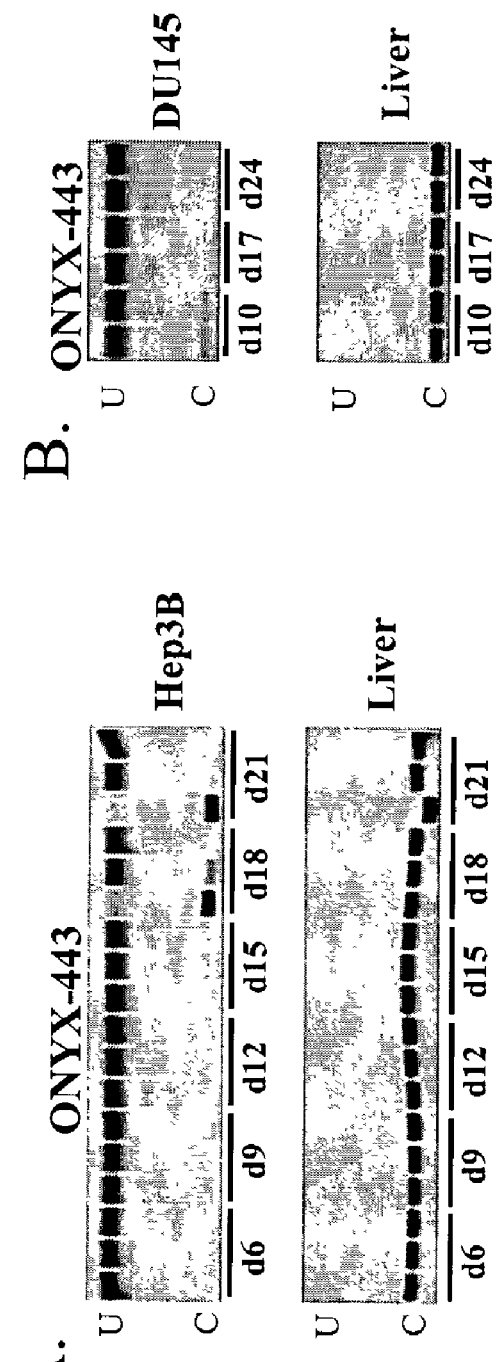
FIG. 6 shows CD expression in Hep3B and DU145 tumor xenografts and the corresponding liver following intravenous injection of ONYX-443. Virus injection and animal sample analysis were performed as described in FIG. 5A. In the Hep3B study ONYX-443 was dosed at $2 \times 10^8$ pfu per day for 5 consecutive days (FIG. 6A). In the DU145 study, ONYX-443 was dosed at $5 \times 10^8$ pfu per day for 5 consecutive days (FIG. 6B). At indicated time points (in days, d), animals were sacrificed, tumors and livers were removed and analyzed for CD enzymatic activity. Each lane represents an individual animal.

CD expression following intravenous virus inoculation was evaluated in other xenograft mouse models, including Hep3B, DU145 and C33A. In Hep3B tumors, CD expression from ONYX-443 was also high (FIG. 6A). The C33A tumor expression pattern was similar to that of the Hep3B model. In DU145 tumors, ONYX-443 demonstrated a sustained high level of CD activity for at least 24 days (FIG. 6B). In contrast, no CD activity was detected in livers from animals injected with ONYX-443. Lung and spleen tissues also had no detectable CD activity following intravenous injection.

Taken together, ONYX-443 has a favorable in vivo heterologous expression profile, displaying superior CD activity level in a variety of tumors as well as better tumor versus liver specificity.

Correlation Between CD Activity, CD Protein Level and Viral Late Gene Expression.

In order to determine whether the CD activity we detected is a reflection of CD protein expression level, we would analyze the animal tumor samples from one typical experiment for both the CD activity and CD protein level. The data would show a correlation between CD enzymatic activity (converting cytosine to uracil) and CD protein, indicating the CD activity assay reflects the CD gene expression level.

We also can determine if CD gene expression is correlated with the replication of ONYX-443, and if so, if the expression of CD is as a late protein. Two experiments could establish that this is the case. First, fiber is a late viral protein whose expression is strictly dependent upon viral DNA replication, and is often used as a marker for adenovirus replication. Therefore we would examine adenovirus fiber expression in tumor samples taken from mice bearing C33A tumors and injected intravenously with ONYX-443 as described in FIG. 5A. At indicated time points, tumor samples are removed and analyzed for CD enzymatic activity using the cytosine-to-uracil conversion assay, and adenovirus fiber protein levels by immunoblotting analysis. The results would show a good correlation between CD activity and fiber expression, showing that CD expression is directly linked to the replication of the viral vectors.

Second, an experiment can be done to show that CD is expressed as an adenoviral late protein. This is done by determining the effects of araC (1-B-D-arabinofuranosylcytosine) on CD expression. An important characteristic of adenoviral late protein expression is that it is dependent on viral DNA synthesis. Thus, an experiment to show bona fide late protein expression is to determine whether or not expression occurs in the presence of araC, an inhibitor of DNA replication.

Thus, araC can be added to the culture medium at a concentration of 20 micrograms per milliter containing A549 cells, such cells are available from the American Type Culture Collection, that are infected with ONYX-443 at an m.o.i. of 10 and cell lysates analyzed by Western blot. The results would show that CD in E3B is a bona fide late protein as its expression is dependent on DNA replication.

The invention now being fully described, it will be apparent to one of ordinary skill in the art that many changes and modifications can be made thereto without departing from the spirit or scope of the appended claims.

---

We claim:

1. An adenoviral vector comprising
   (i) an E2F responsive transcriptional nucleotide regulatory binding site that controls the expression of an adenoviral early gene,
   (ii) an endogenous adenoviral E3 region promoter, and
   (iii) a heterologous gene inserted in the E3 region of the adenoviral vector, wherein the heterologous gene is heterolorous to the adenoviral vector and operably linked to the endogenous adenoviral E3 region promoter.

2. The adenoviral vector of claim 1, wherein the adenoviral early gene is an immediate early gene.

3. The adenoviral vector of claim 2, wherein the transcriptional nucleotide regulatory binding site is a promoter.

4. The adenoviral vector of claim 3, wherein the E2F responsive promoter is substituted for an endogenous adenoviral E1a promoter.

5. The adenoviral vector of claim 3, wherein the E2F responsive promoter is substituted for an endogenous adenoviral E4 promoter.

6. The adenoviral vector of claim 5, wherein the adenoviral vector further comprises nucleotide regulatory sites that substantially facilitate adenoviral replication comprising Sp1, ATF, NF1 and NFIII/Oct-1.

7. An adenoviral vector comprising
   (i) an adenoviral transcriptional nucleotide regulatory binding site that controls the expression of an adenoviral early gene, wherein the site is inactivated by the insertion of an E2F responsive transcriptional nucleotide regulatory binding site such that the E2F responsive transcriptional nucleotide regulatory binding site controls the expression of the adenoviral early gene,
   (ii) an endogenous adenoviral E3 region promoter, and
   (iii) a heterologous gene inserted in the E3 region of the adenoviral vector, wherein the heterologous gene is heterologous to the adenoviral vector and operably linked to the endogenous adenoviral E3 region promoter and is heterologous to the adenoviral vector.

8. The adenoviral vector of claim 7, wherein the adenoviral early gene is an immediate early gene.

9. The adenoviral vector of claim 8, wherein the inactivated transcriptional nucleotide regulatory binding site is a promoter.

10. The adenoviral vector of claim 9, wherein the inactivated transcriptional nucleotide regulatory binding site is an endogenous adenoviral E1a promoter.

11. The adenoviral vector of claim 9, wherein the inactivated transcriptional nucleotide regulatory binding site is an endogenous adenoviral E4 promoter.

12. The adenoviral vector of claim 11, wherein the inactivated transcriptional nucleotide regulatory binding site further comprises an endogenous adenoviral E1a promoter.

13. The adenoviral vector of claims 1 or 7, wherein the transcriptional nucleotide regulatory sequence that is E2F responsive is human E2F-1.

14. The adenoviral vector of claim 13, wherein the heterologous gene is inserted in an E3 region of the adenoviral genome that is expressed late during the replication phase of the viral vector.

15. The adenoviral vector of claim 14, wherein the heterologous gene is inserted in the E3b region of the virus.

16. The adenoviral vector of claim 13, wherein the adenoviral vector is a replication deficient virus.

* * * * *